United States Patent [19]

Kotani et al.

[11] Patent Number: 4,863,493
[45] Date of Patent: Sep. 5, 1989

[54] HIGH PURITY ACETYLENE GAS

[75] Inventors: Yasuo Kotani, Hirakata; Kengi Yamawaki, Sakai; Minoru Nishida, Kobe, all of Japan

[73] Assignee: Nichigo Acetylene Kabushiki Kaisha, Osaka, Japan

[21] Appl. No.: 148,794

[22] Filed: Jan. 27, 1988

[30] Foreign Application Priority Data

Aug. 7, 1987 [JP] Japan .................. 62-198498

[51] Int. Cl.$^4$ ............................. B01D 53/14
[52] U.S. Cl. .......................... 55/20; 55/35; 55/48; 55/64; 55/66; 55/74; 55/220; 55/228; 55/387
[58] Field of Search ............... 55/63–65, 55/74, 387; 206/0.6, 0.7; 220/3

[56] References Cited

U.S. PATENT DOCUMENTS

| | | | |
|---|---|---|---|
| 1,181,116 | 5/1916 | Curme, Jr. ................ | 55/63 |
| 1,230,531 | 6/1917 | Stephenson ................ | 206/0.7 X |
| 1,906,035 | 4/1933 | Wulff ................ | 206/0.7 X |
| 2,146,448 | 2/1939 | Scott et al. ................ | 55/63 X |
| 2,422,251 | 6/1947 | O'Brian et al. ................ | 206/0.7 |
| 3,376,693 | 4/1968 | Rinaldi et al. ................ | 55/65 |
| 3,594,988 | 7/1971 | Eisenlohr et al. ................ | 55/64 |
| 3,695,002 | 10/1972 | Rottmayr et al. ................ | 55/64 |
| 3,706,181 | 12/1972 | Walker et al. ................ | 55/63 |
| 3,775,507 | 11/1973 | Duembgen et al. ................ | 55/63 X |
| 3,816,976 | 6/1974 | Stork et al. ................ | 55/64 X |
| 3,837,144 | 9/1974 | Lewis ................ | 55/64 |
| 3,870,482 | 3/1975 | Walker et al. ................ | 55/63 X |
| 4,086,288 | 4/1978 | Irvin et al. ................ | 55/64 X |
| 4,177,250 | 12/1979 | Irvin et al. ................ | 55/64 X |
| 4,349,463 | 9/1982 | Flanigen ................ | 206/0.7 X |
| 4,655,798 | 4/1987 | Ruch et al. ................ | 55/64 |

FOREIGN PATENT DOCUMENTS

| | | | |
|---|---|---|---|
| 13081 | 4/1973 | Japan ................ | 55/63 |
| 158288 | 7/1962 | U.S.S.R. ................ | 55/63 |
| 950971 | 3/1964 | United Kingdom ................ | 55/63 |

Primary Examiner—Robert Spitzer
Attorney, Agent, or Firm—Armstrong, Nikaido, Marmelstein, Kubovcik & Murray

[57] ABSTRACT

High purity acetylene gas is provided by discharging high purity acetylene gas from a metallic bomb in which a porous material to accommodate high purity acetylene gas and a solvent to selectively dissolve the acetylene gas are charged and passing the gas through an adsorber containing an adsorbent for adsorbing the solvent contained in the gas. Superfine powders of impurities are removed by passing the gas through a filter. Acetylene is purified by adsorbing acetylene into a solvent having a temperature of $-20°$ to $-81.8°$ C. in an absorbing tower, stripping the acetylene from the solvent at a temperature of $-10°$ to $+20°$ C. in a stripping tower and passing the stripped acetylene through a packed bed filled with a porous material for removing impurities from the acetylene and through a filter for removing superfine powders of impurities. The inside of a bomb for dissolved acetylene is purified by heating the bomb and evacuating the bomb. A bomb for acetylene charged with a solvent which selectively dissolves acetylene is filled with high purity acetylene gas by thermostatically controlling the temperature of the bomb at a low temperature and filling the bomb with acetylene gas without the use of pressure.

14 Claims, 3 Drawing Sheets

HIGH PURITY ACETYLENE GAS

BACKGROUND OF THE INVENTION

The present invention relates to a process for providing high purity acetylene gas obtained from dissolved acetylene which is charged in a dissolved acetylene bomb and an apparatus used in the process, a process for purifying acetylene and an apparatus used in the process, a process for purifying the inside of a bomb for dissolved acetylene and a process for charging high purity acetylene into a bomb, and more particularly to a process for purifying the inside of a bomb for high purity dissolved acetylene, which is used as a bomb for storing and supplying high purity dissolved acetylene being employed as a source material used for a functional thin film having a crystal structure such as Si—C structure or diamond cubic, which is used in a high efficiency semi-conductor, an electron device, and the like, and a process for charging high purity acetylene rapidly and safely into a bomb while maintaining the purity.

Conventionally, acetylene has hitherto been employed as a raw material in the field of acetylene welding or in the chemical industry.

Acetylene which is employed as a raw material in the field of acetylene welding or chemical industry is prepared from calcium carbide or petroleum. The crude acetylene such as carbide acetylene which is prepared from calcium carbide or petroleum acetylene which is prepared from petroleum just after the preparation, is purified to remove impurities such as $PH_3$, $H_2S$, $NH_3$ and $AsH_3$ which are harmful for health or which deteriorate the mechanical strength of a weld zone when the acetylene is employed for welding and to remove impurities such as $O_2$, $PH_3$ and $H_2S$ which are catalyst poisons in a chemical reaction and to give purified acetylene having a purity of not less than 98% by volume which is prescribed in JIS (Japanese Industrial Standards) K 1901 and JIS K 1902.

For instance, in dissolved acetylene which is prepared from commercially available calcium carbide, acetylene is contained in a content of 98.0 to 99.5% by volume and as the other components, impurities such as vapour of solvent, nitrogen, oxygen and argon which come from air are contained as main impurities and impurities such as $NH_3$, $PH_3$, $H_2S$, hydrogen and $CH_4$ which come from calcium carbide are contained as the other impurities. It is reported from Osaka Kankyo Gijutsu Center that as one result of the analysis of dissolved acetylene, the dissolved acetylene contains acetylene of 99.10% by volume, a solvent, i.e., acetone of 0.38% by volume, hydrogen of 0.01% by volume, nitrogen of 0.2844% by volume, oxygen of 0.0756% by volume, CO of less than 0.01% by volume, $CO_2$ of less than 0.01% by volume and $CH_4$ of 0.13% by volume.

Commercially available petroleum acetylene contains acetylene in a content of about 99.5% by volume and impurities such as $C_2H_4$ and $CO_2$.

With the progress of technology, recently, new materials have been produced from acetylene. For instance, acetylene has been employed as a source material of polyacetylene which is a conductive organic material or an acetylene derivative which is a photosensitive organic material. Also, acetylene which has high reactivity has been employed as a source material of carbon contained in a carbide having a high purity which is employed as functional materials being called fine ceramics or as source materials for producing a-SiC:H having a high conversion efficiency of solar energy, which is sometimes employed as a window layer of a-Si solar cells.

There is a necessity to strictly control the components of a material in order to give a material having required properties. Therefore, acetylene having a high purity which can be used as a source material has been required.

In a dissolved acetylene bomb, i.e., a bomb for dissolved acetylene, conventionally, calcium silicate having a stable physical property is filled in a form of semi-crystal which is a so-called mass in a content of not more than 10% by volume of the content volume of the dissolved acetylene bomb. The mass in the dissolved acetylene bomb generally has a porosity of not less than 90% by volume. The mass is a porous material which is prepared by filling a dissolved acetylene bomb with a mixture of raw materials comprising calcium silicate as a main component and the like and a prescribed amount of water and heating the bomb in a heating furnace to react the mixture. In the space and on the inside wall of the dissolved acetylene bomb, small amounts of impurity gases such as nitrogen gas, oxygen gas, water vapour and carbon dioxide gas, water, and the like, which are introduced, e.g., when the mass is formed and the bomb is subjected to airtightness test with air having a pressure of about 28 atoms which is 1.1 times that of working pressure, are contained.

In case that the bomb is newly employed as a bomb for acetylene, since it is not preferable that impurity gas, in particular, oxygen gas is contained in the bomb, so-called a process for washing with purified acetylene gas, that is, after purified acetylene is charged into a bomb under a pressure of about 3 $Kg/cm^2.G$ and the bomb is allowed to stand, residual impurity gas or vapour contained in the bomb is liberated with the acetylene gas to purify the inside of the bomb when the dissolved acetylene is gasified and liberated. The cleanliness of the inside of the bomb is determined by analyzing the liberated gases and vapours and measuring the concentration of the acetylene gas. The standard of cleanliness is that the concentration of acetylene gas is not less than 98.0% by volume as mentioned above.

As a process for charging acetylene gas into a bomb in which a solvent which selectively dissolves acetylene is charged, conventionally, a process that acetylene gas is pressured with a compressor and the pressured acetylene gas is charged into the bomb by the difference between the pressure of the pressured acetylene gas and the internal pressure of the bomb.

According to the above process, it takes 6 to 8 hours to charge acetylene gas into a bomb under a pressure of 20 to 25 $Kg/cm^2.G$ to satisfy the legal standard for charging acetylene, that is, the internal pressure of the bomb should be not more than 15.5 $Kg/cm^2.G$ at 15° C. since the temperature of the acetylene is increased by pressing the acetylene at ordinary temperature and the temperature of the acetylene is further increased by the heat of dissolution of the acetylene when the acetylene is dissolved into a solvent in a bomb, and thereby the inside temperature of the bomb is increased and the solubility of acetylene is lowered although the temperature of acetylene is somewhat decreased by sprinkling the bomb with water.

As a process for preparing purified acetylene which is used in new materials, a process for preparing purified acetylene comprising removing a solvent with a low temperature trap or an adsorbent such as silica gel, cooling acetylene to not more than about −150° C. to give solid acetylene with a bath of liquid nitrogen, removing vapours contained in the trap by evacuating the trap and vaporizing impurities contained in the solid acetylene is well-known. The process is suitable for being used in a small scale laboratory but there is a risk for explosive decomposition when the absolute pressure of the trap is not less than 1.4 Kg/cm$^2$. Therefore, the process is not suitable for safely and economically providing acetylene in an industrial necessary amount.

First of all, the object of the present invention is to provide a process for providing high purity acetylene gas, comprising transporting purified acetylene gas safely in a necessary amount for industrial uses to a place where the acetylene gas is used and preparing high purity acetylene at the place.

Second, the object of the present invention is to provide purified acetylene safely in a necessary amount for industrial uses.

Also, according to a conventional process for purifying the inside of a dissolved acetylene bomb, it is difficult to remove residual impurity gases such as nitrogen gas and oxygen gas contained in the space of the bomb and to reduce the content of impurity gases to an order of not more than ppm to give a highly purified bomb, and there is a problem that the concentration of residual impurity gases which are not dissolved in a solvent such as nitrogen gas and oxygen gas remained in the space, the mass and the like of the bomb is increased to about 100 to 300 ppm when the bomb is allowed to stand for several days although the inside of the bomb is purified to give acetylene having an apparent purity of 5N (five nine), that is, 99.999% by volume in the middle course of liberating when the inside of the bomb is cleaned with acetylene repeatedly.

As mentioned above, a dissolved acetylene bomb which can accommodate and supply high purity acetylene with keeping the purity has not yet been developed. Accordingly, the development of a bomb for high purity dissolved acetylene has been eagered in the present technical field.

Third, the object of the present invention is to provide a bomb for high purity dissolved acetylene.

Also, according to a conventional process for charging acetylene gas into a bomb, there are following problems.

(a) Since acetylene is a chemically unstable compound and there is a risk to generate explosive decomposition when acetylene is abruptly pressured, the acetylene is pressured so that the compression ratio is not more than 3. However, it takes a long time, that is, 6 to 8 hours for charging, e.g., a prescribed amount of acetylene (7.2 Kg) into a bomb (content volume:41 l) which is usually employed, and further, since the final pressure when acetylene is charged into a bomb is high, that is, 20 to 25 Kg/cm$^2$.G, acetylene is in extremely unstable and dangerous state.

(b) In case that acetylene gas is charged into a bomb, since a compressor is employed, there is a necessity to use a series of equipment such as an oil separator, a high pressure drier, and the like. Further, there are problems that it is difficult to replace residual air in the series of the equipment with acetylene which is beforehand purified, that a large amount of acetylene gas for replacing is needed, that it takes a long time for replacing and that it is difficult to keep the purity of the equipment.

Fourth, the object of the present invention is to provide a process for filling a bomb with high purity acetylene gas to solve the above problems.

SUMMARY OF THE INVENTION

According to the present invention, first of all, there are provided a process for providing high purity acetylene gas, comprising discharging high purity acetylene gas from a dissolved acetylene bomb and removing a solvent which accompanies the high purity acetylene gas by passing the high purity acetylene through an adsorbent and a filter when the acetylene is used, and an apparatus for purifying high purity acetylene, comprising a metallic bomb in which a porous material to accomodate high purity acetylene gas and a solvent to selectively dissolve the acetylene gas are charged, an adsorber which adsorbs a solvent accompanying the acetylene when the acetylene is used and a filter for removing superfine powders of impurities, wherein the metallic bomb is connected with the adsorber and the filter is equipped at the outlet of the adsorber.

Second, there is provided a process for purifying acetylene, comprising absorbing acetylene into a solvent having a temperature of −20° to −81.8° C., heating the solvent containing the acetylene, stripping the acetylene and passing the stripped acetylene through a packed bed in which a porous material is filled and through a filter for removing superfine powders of impurities, and an apparatus for purifying acetylene, comprising an acetylene absorbing tower for absorbing acetylene into a solvent which selectively absorbs acetylene at −20° to −81.8° C., an acetylene stripping tower for stripping the acetylene at −10° to +20° C., an adsorbing tower for removing impurities included in the acetylene, in which porous materials are filled, a filter for removing superfine powders of impurities, an equipment for carrying the solvent in which acetylene is absorbed from the acetylene absorbing tower to the acetylene stripping tower and an equipment for returning the solvent from which acetylene is stripped from the acetylene stripping tower to the acetylene absorbing tower.

Third, according to the present invention, there is provided a process for purifying the inside of a dissolved acetylene bomb for storing acetylene, comprising heating a dissolved acetylene bomb and evacuating the dissolved acetylene bomb.

Fourth, according to the present invention, there is provided a process for filling a bomb with high purity acetylene gas, comprising thermostatically controlling the temperature of a bomb at a low temperature to fill the bomb with acetylene gas without any pressing method when filling a bomb in which a solvent which selectively dissolves acetylene is charged, with high purity acetylene gas.

DETAILED DESCRIPTION

First of all, a process for providing high purity acetylene gas and an apparatus for purifying high purity acetylene used in the process are explained below.

It has been found that most of the impurity gases exist in the space of a dissolved acetylene bomb and that coconut husk activated carbon can efficiently adsorb and remove vapour of a solvent from the mixture of acetylene and vapour of a solvent.

According to the present invention, high purity acetylene gas can be obtained by a process comprising absorbing acetylene into a solvent which selectively absorbs acetylene, removing impurity gases, which have a lower solubility than the acetylene contained in the space of a bomb, from the acetylene with the change of solubility which is caused by the change of pressure of the bomb to improve the purity of the residual acetylene in the bomb and passing the vapour of solvent accompanied with the acetylene gas through a packed bed of coconut husk activated carbon (hereinafter referred to as "adsorber") to adsorb and remove the vapour of solvent when the residual acetylene is used.

In the present invention, any acetylene can be employed. Examples of the acetylene are, for instance, crude acetylene prepared from calcium carbide or petroleum, acetylene which is purified to remove $PH_3$, $H_2S$, $NH_3$, $AsH_3$, and the like so as to satisfy JIS K 1901 and JIS K 1902, and the like. The present invention is not limited by the purity, kinds of the raw material, and the like of acetylene. However, from the viewpoint of giving purified acetylene efficiently, when acetylene which is prepared from calcium carbide is employed, it s preferable that the acetylene is pretreated by a process for purifying acetylene which is disclosed in the specification of Japanese Patent No. 203622, and the like.

The term "high purity acetylene" in the specification means acetylene containing impurities in a content of less than 100 ppm. One example of the high purity acetylene is acetylene having a composition that the content of hydrogen is not more than 1 ppm, the content of oxygen is 1.0 to 15.0 ppm, the content of nitrogen is 1.0 to 25.0 ppm, the content of CO is not more than 1.0 ppm, the content of $CO_2$ is not more than 2.0 ppm and the contents of $H_2S$, $PH_3$, $AsH_3$ and a solvent are not detected when the contents of impurities contained in the acetylene are analyzed under the detection limit of 0.1 ppm.

The acetylene is absorbed into a solvent and the mixture of the acetylene and the solvent is charged into a dissolved acetylene bomb by a usual process for filling a bomb with acetylene employed in a factory for preparing dissolved acetylene.

As a solvent, any kinds of solvent can be employed if the solvent selectively absorbs acetylene and does not react with acetylene. Examples of the solvent are, for instance, acetone having a high selective absorptivity of acetylene, N,N-dimethylformamide (hereinafter referred to as "DMF"), N-methylpyrrolidone, and the like. These solvents can be employed alone or in admixture thereof.

After the dissolved acetylene bomb in which acetylene is charged is allowed to stand for a day and night so as that the solubility of acetylene in the solvent is constant and the dissolved acetylene bomb is mounted on a weighing machine, 20 to 80% by weight of acetylene charged in the bomb is discharged by opening a vessel valve while measuring the change of weight of the bomb. When the discharged amount of acetylene is less than 20% by weight, the content of impurities contained in the acetylene in the space of the dissolved acetylene bomb is more than 100 ppm and when the discharged amount of acetylene is more than 80% by weight, it is not preferable for practical use and it is uneconomical since the amount of acetylene which can be used is decreased.

The acetylene in the dissolved acetylene bomb prepared by the above-mentioned process contains a small amount of impurities. However, since the acetylene contains a solvent such as acetone or DMF, the acetylene is passed through an adsorber which selectively adsorbs the vapour of solvent.

In comparison with the adsorptivity of a conventional adsorbent such as a molecular sieve or silica gel which is used as an adsorbent for adsorbing a solvent contained in air, coconut husk activated carbon shows extremely larger adsorptivity in the acetylene-solvent system as shown in Table 1. Therefore, the coconut husk activated carbon can be particularly preferably used in the present invention.

TABLE 1

| Adsorbent (100 g) | Amount of adsorbed solvent (acetone) contained in acetylene (g) (at 25° C.) |
|---|---|
| Coconut husk activated carbon | 14.0 |
| Molecular sieve (13X)*1 | 0.5 |
| Silica gel | 0.6 |

(Note)
*1: Available from UNION CARBIDE CORP.

Further, a porous material prepared from a molecular sieve, silica gel, or the like other than the coconut husk activated carbon can be properly added into the adsorber in order to remove humidity.

In the present invention, coconut husk activated carbon which is crushed to have a particle size of 4 to 8 mesh is usually employed. When an adsorber in which coconut husk activated carbon not subjected to pretreatment is employed, since air including nitrogen, oxygen and the like, which is contained in the coconut husk activated carbon, is mixed with acetylene at the time that acetylene is passed through the adsorber and the purity of acetylene is lowered, there is a necessity that the coconut husk activated carbon is subjected to pretreatment before acetylene is passed through the coconut husk activated carbon.

Therefore, it is preferable that the coconut husk activated carbon is subjected to the pretreatment that the coconut husk activated carbon is washed by passing hydrogen gas, helium gas or superheated steam having a high temperature through the coconut husk activated carbon. Examples of the pretreatment are, for instance, a process that before acetylene is passed through an adsorber, the adsorber is heated to 200° to 300° C. and is evacuated with a pump such as a rotary pump or a vacuum pump while passing hydrogen gas at a flow rate of 100 to 200 ml/minute through the adsorber and then purified acetylene gas is passed through the adsorber to replace the hydrogen gas with purified acetylene.

The amount of acetylene which is passed through the adsorber, the residence time of the acetylene in the adsorber, and the like are properly adjusted in consideration of the aimed purity of acetylene, the refining efficiency, and the like. However, it is preferable that the volume of acetylene which is passed through the adsorber is usually 10000 times as much as the volume of coconut husk activated carbon per one hour.

According to the above process, for instance, acetylene having a purity of 98 to 99.5% by volume can be purified to acetylene having a purity of about 99.99 to 99.9999% by volume.

Figure 1:
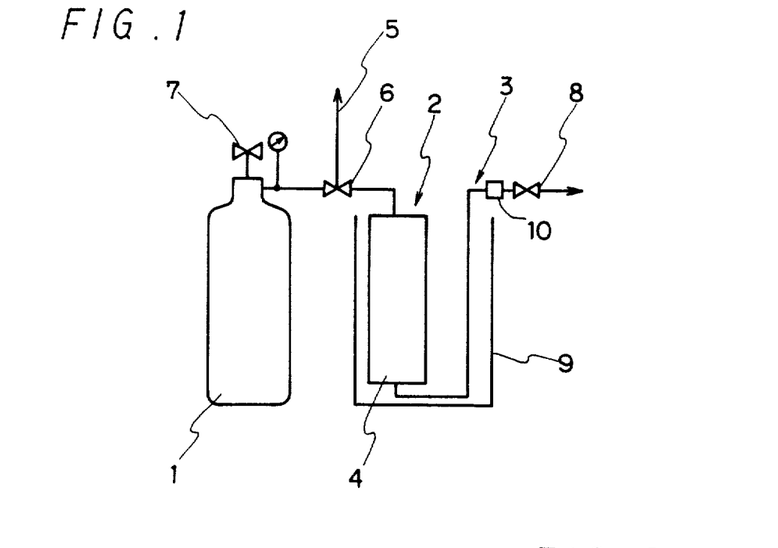
FIG. 1 is a drawing explaining one embodiment of an apparatus employed in the process for providing high purity acetylene gas of the present invention.

The process for providing high purity acetylene gas and the apparatus used in the process of the present invention are explained on the basis of FIG. 1.

The apparatus for purifying acetylene comprises a dissolved acetylene bomb 1 in which acetylene dissolved in a solvent is charged, an inflow port for gas 2 and an adsorber 4 having an outflow port for gas 3, and the dissolved acetylene bomb 1 is connected with the inflow port for gas 2 of the adsorber 4 through a change valve 6 having an opening for gas 5.

It is preferable that the inside of the dissolved acetylene bomb 1 is purified before acetylene and a solvent are charged into the dissolved acetylene bomb 1 since the amount of residual impurities is decreased and the purity of the inside of the dissolved acetylene bomb 1 is improved. The process for purifying the inside of the dissolved acetylene bomb 1 is explained below.

The change valve 6 is changed so that the dissolved acetylene bomb 1 in which acetylene dissolved in a solvent is filled is connected with the opening for gas 5 to liberate the mixture of acetylene gas and vapour of the solvent in an amount of 20 to 80% by weight based upon the amount of the mixture in the dissolved acetylene bomb 1. The residual mixture of the acetylene gas and the vapour of the solvent is passed through the adsorber 4 to adsorb and remove the vapour of the solvent by changing the change valve 6 so that the dissolved acetylene bomb 1 is connected with the adsorber 4 and opening the vessel valve 7 and the gas-effluent valve 8, and thereby acetylene gas having high purity is obtained.

The acetylene dissolved in a solvent which is contained in the dissolved acetylene bomb 1 can be liberated in an amount of 20 to 80% by weight based upon the amount of the mixture in the bomb 1 from the opening for gas by changing the change valve 6 to connect the dissolved acetylene bomb 1 with the opening for gas 5. Also, the mixture of the acetylene gas and the vapour of the solvent can be liberated in an amount of 20 to 80% by weight based upon the amount of the mixture in the dissolved acetylene bomb 1 before the dissolved acetylene bomb 1 is connected with the inflow port for gas 2. In this case, liberated acetylene can be recovered and reused by connecting the opening 5 with an apparatus for recovering acetylene.

When the gas-effluent valve 8 is left to be opened, since coconut husk activated carbon in the adsorber 4 sometimes adsorbs air which is entered from the gas-effluent valve 8, the gas-effluent valve 8 should be shut except when the adsorber 4 is used.

Further, it is preferable that before the adsorber 4 is used, impurity gases such as nitrogen gas and oxygen gas which are adsorbed into the coconut husk activated carbon in the adsorber 4 are removed by heating the adsorber 4 in a heating system 9 while the vessel valve 7 is closed and high purity hydrogen gas is carried into the adsorber 4 from the opening for gas 5 by changing the change valve 6 to connect the adsorber 4 with the opening for gas 5 in order to improve the purity of acetylene.

In addition to the above process, it is preferable that a filter for removing superfine powders of impurities and a solvent 10 such as ULF type filter commercially available from Nippon Paionikusu Company is equipped between the adsorber 4 and the gas-effluent valve 8. For example, when the filter 10 is applied, superfine powders having a particle size of 0.09 $\mu$m can be removed to an order of not more than $10^{-8}$%. The above procedure can be applied to the following processes.

Next, the process for purifying acetylene and the apparatus used in the process of the present invention are explained below.

According to the present invention, high purity acetylene is prepared by absorbing acetylene into a solvent which selectively absorbs acetylene and stripping the solvent containing the acetylene with the difference of the solubility of the acetylene and the solvent, which is caused by temperature change, in a batch system or a continuous system.

As the acetylene which is absorbed into a solvent which selectively absorbs acetylene, the abovementioned acetylene can be employed.

The temperature when acetylene is absorbed into a solvent should be adjusted to be in a range of $-20°$ to $-81.8°$ C. from the viewpoint that the dissolved amount and dissolved rate of the acetylene into the solvent are increased and the acetylene is economically absorbed into the solvent without the acetylene being liquified (the liquified temperature of acetylene is $-81.8°$ C. under the pressure of 760 mmHg), and it is preferable that the temperature when acetylene is absorbed into a solvent is in a range of $-40°$ to $-60°$ C. When the temperature is higher than $-20°$ C., the purity of the purified acetylene is less than about 99.9% by volume.

The pressure when acetylene is absorbed into a solvent is not particularly limited if the absolute pressure is not more than 7.0 kg/cm$^2$ which means that there is little possibility to generate explosive decomposition of acetylene when the acetylene coexists with a solvent. However, the range of the pressure is usually determined by the kinds of raw material of the acetylene. In general, the pressure is adjusted with a pressure regulator so that, for instance, when the acetylene is carbide acetylene or petroleum acetylene, the absolute pressure is about 1.02 to 1.5 kg/cm$^2$ and when the acetylene is dissolved acetylene, the absolute pressure is about 1.2 to 1.5 kg/cm$^2$.

There is no limitation for the kinds of the solvent which absorb acetylene selectively if the solvent is liquid when the solvent is in the condition mentioned above and does not react with acetylene and purified acetylene can be prepared by stripping acetylene at a temperature of $-10°$ to $+20°$ C., preferably $-5°$ to $+5°$ C. Examples of the solvent are, for instance, acetone having a high selective absorptivity of acetylene, DMF, N-methylpyrrolidone. The solvents may be employed alone or in admixture thereof.

The term "absorb acetylene selectively" means that there is a remarkable difference between the solubility of impurities such as $O_2$, $N_2$, CO and $H_2$ which are contained in acetylene and that of acetylene. For instance, in case that the solvent is DMF, there is a difference as shown in Table 2. The amount of acetylene dissolved in a solvent depends on the temperature of the solvent. Usually increasing the temperature tends to decrease the solubility. For instance, when 1 l of DMF saturated with acetylene having a temperature of −40° C. is heated to 0° C., about 238 l of acetylene at S.T.P. is stripped from DMF, and when 1 l of DMF saturated with acetylene having a temperature of −60° C. is heated to 0° C., about 382 l of acetylene at S.T.P. is stripped from DMF. As mentioned above, the terminology "stripped acetylene" is intended to refer to "acetylene stripped from a solvent".

TABLE 2

| Gas | Solubility (l/l at 25° C.) |
| --- | --- |
| $C_2H_2$ | 31.4 |
| $H_2$ | 0.04 |
| $N_2$ | 0.04 |
| $O_2$ | 0.11 |
| CO | 0.06 |
| $CO_2$ | 4.5 |
| $CH_4$ | 0.32 |

(Note)
The above data are described in a catalogue relating to DMF available from NITTO CHEMICAL INDUSTRY CO., LTD.

It is economically preferable that the stripping temperature of acetylene absorbed in a solvent is −10° to +20° C. since the difference of solubility between the acetylene and impurities is large, which is caused by the difference between the temperature when acetylene is absorbed and the temperature when acetylene is stripped, and thereby the efficiency for recovering acetylene is improved. In particular, from the viewpoint of efficiency of thermal energy, it is preferable that the stripping temperature is about −10° to 0° C. and from the viewpoint of purified amount of acetylene, it is preferable that the stripping temperature is 0° to +10° C.

Also, it is preferable that the absolute pressure of acetylene when acetylene is stripped is 1.0 to 1.3 kg/cm². When the pressure is less than 1.0 kg/cm², air can be introduced into the acetylene and when the pressure is more than 1.3 kg/cm², there is a possibility that explosive decomposition of acetylene is generated.

Since the purified acetylene is not liquified and contains a solvent which is employed when the acetylene is purified, in order to absorb and remove impurities and the vapour of solvent coexisting with the acetylene, it is preferable that the purified acetylene is cooled to a temperature of −50° to −81.8° C. and is passed through a packed column in which porous materials are filled.

Examples of the above-mentioned packed column in which porous materials are filled are usual packed towers which can be cooled, for instance, a cylinder in which a porous material having a particle size of 4 to 14 mesh and a pore diameter of about 4 to 13 Å such as activated carbon, molecular sieve or silica gel are filled.

The amount of acetylene which is passed through a packed column in which porous materials are filled and the residence time of acetylene can be usually determined in consideration of the purity of obtained acetylene and the efficiency of purification. It is preferable that the amount of acetylene which is passed through the packed column is usually not more than 10000 times that of the porous material per one hour.

According to the above process, for instance, acetylene having a purity of 98 to 99.5% by volume can be purified to acetylene having a purity of about 99.99 to 99.9999% by volume.

The purified acetylene can be employed as it is or can be charged into a bomb. Further, when highly purified acetylene having a purity of not less than $9^7$, that is, seven-nine (99.99999% by volume) is needed, it is preferable that the purified acetylene is refined by repeating the above-mentioned process.

Figure 2:
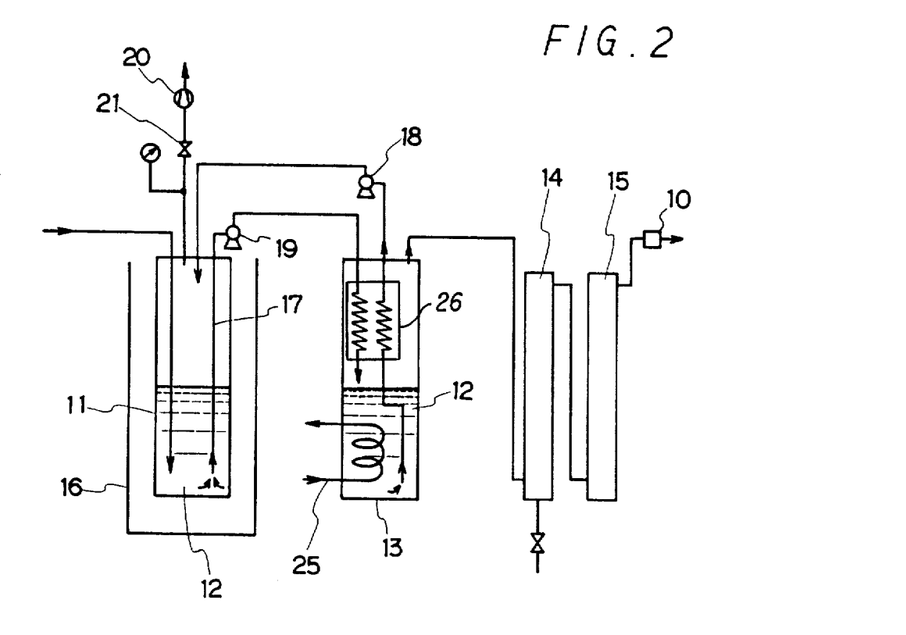
FIG. 2 is a drawing explaining one embodiment of an apparatus employed in the process for purifying acetylene of the present invention and FIG. 3 is a drawing explaining another embodiment of an apparatus employed in the process for purifying acetylene of the present invention.
Figure 3:
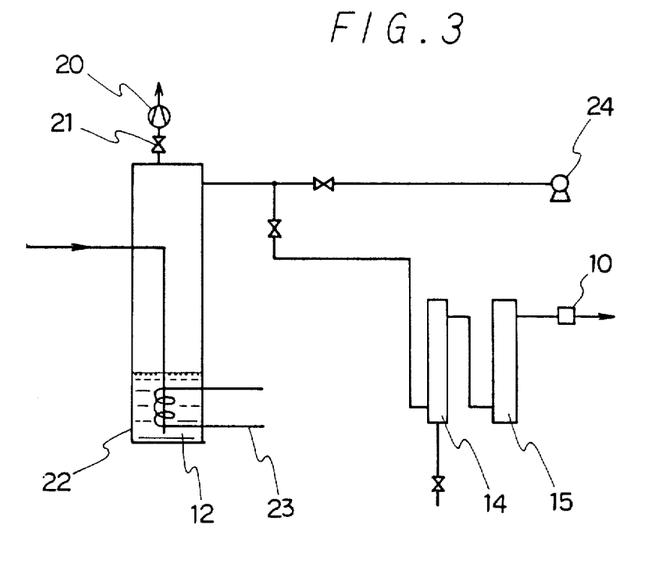

The process of the present invention can be carried out in a batch system, that is, the absorption process and stripping process of acetylene are carried out in the same tower as shown in FIG. 3 or in a continuous system, that is, acetylene is purified by a continuous process comprising absorbing acetylene into a solvent in a tower, carring the solvent in which the acetylene is absorbed to another tower and stripping the acetylene in the another tower as shown in FIG. 2.

Next, the process for purifying acetylene of the present invention is explained on the basis of FIG. 2.

(Absorbing process)

(1) Acetylene absorbing solvent 12 contained in an acetylene absorbing tower 11 is cooled to a temperature of −20° to −81.8° C. (by dipping the acetylene absorbing tower 11 into a cooling pool 16) to absorb acetylene into the acetylene absorbing solvent 12. The heat generated when the acetylene is absorbed into the solvent 12 is removed by the cooling pool 16 and the temperature of the acetylene absorbing solvent 12 is adjusted to be a prescribed temperature in the range of −20° to −81.8° C.

The acetylene is introduced into the acetylene absorbing solvent 12 at the lower portion of the acetylene absorbing solvent 12 in the acetylene absorbing tower 11 and the acetylene is absorbed into the acetylene absorbing solvent 12 when the acetylene is carried upward.

(2) As the acetylene absorbing solvent 12, a solvent which dissolves acetylene is employed. Most of impurity gases such as $O_2$, $N_2$, CO and $H_2$ exist in the space of the tower 11 and little of the impurity gases is absorbed into the acetylene absorbing solvent 12. The impurity gases are exhausted with acetylene from an outfall 20 by opening a blowdown valve 21.

(3) The cooling of the acetylene absorbing solvent 12 is carried out by adding methanol and dry ice into the cooling pool 16 or by providing a cooling pipe in the acetylene cooling tower 11 and passing a coolant such as an aqueous solution of ethylene glycol through the cooling pipe.

(4) The acetylene absorbing solvent 12 in which acetylene is absorbed and is dissolved is transferred to an acetylene stripping tower 13 at a temperature of −20° to −81.8° C., for instance, by means of a pipe 17 which is provided under the surface of the solvent 12 and a constant rate pump 19 or by means of the pipe 17 and a flow control valve and adjusting of the pressure of the acetylene absorbing tower 11 so that the pressure is larger than that of the acetylene stripping tower 13 in order to avoid that impurity gases existing in the space of the acetylene absorbing tower 11 are mixed with acetylene.

(Stripping process)

(1) The acetylene absorbing solvent 12 which is transferred to the acetylene stripping tower 13 is heated to a temperature of about −10° to +20° C. to strip acetylene from the acetylene absorbing solvent 12 with the change of solubility of acetylene caused by the change of the temperature.

(2) It is preferable from the viewpoint of heat efficiency that the acetylene absorbing solvent having a temperature of −20° to −81.8° C., which is introduced from the acetylene absorbing tower 11 into the acetylene stripping tower 13 and the acetylene absorbing solvent having a temperature of −10° to +20° C., which is returned to the acetylene absorbing tower 11 with a constant rate pump 18 are carried to a heat exchanger 26 which is provided at the upper portion of the acetylene stripping tower 13, in order to exchange the heat.

(3) It is important from the viewpoint of safety to prevent the increase of the internal pressure of the tower 13 as well as economically preferable from the viewpoint of heat efficiency that the acetylene is gradually stripped at a constant rate from the acetylene absorbing solvent. The heat exchange is carried out in the acetylene stripping tower 13, and the acetylene which is stripped from the acetylene absorbing solvent 12 by the increase of temperature is recovered through a cooling tower 14 and an adsorbing tower 15.

(4) It is preferable that the acetylene absorbing solvent which is passed through a heat exchanger 26 provided equipped at the upper portion of the acetylene stripping tower 13, is carried to the acetylene stripping tower 13 and the acetylene absorbing solvent is heated to a prescribed temperature in a range of −10° to +20° C., if necessary, with a heat exchanger for heating 25 in which an antifreeze solution such as 10% aqueous solution of ethylene glycol is circulated, to strip acetylene.

(5) A part of acetylene absorbing solvent is pumped up through a pipe of which opening is dipped into the acetylene absorbing solvent 12 with a constant rate pump 18 and is carried to the upper portion of the acetylene absorbing tower 11. It is preferable that the acetylene absorbing solvent is passed through the abovementioned heat exchanger 26. Then, while adjusting the amount of the acetylene absorbing solvent 12 in the acetylene absorbing tower 11 to be constant, the abovementioned process for absorbing and the above-mentioned process for stripping are continuously carried out. (Process for removing vapour of solvent and the like)

Since the acetylene which is stripped in the acetylene stripping tower 13 contains vapour of a solvent in a content of about 30 to 180 ppm, the acetylene is conducted to a cooling tower 14. It is preferable that silica gel, fine wire of stainless steel or the like is filled in the cooling tower 14 in order to improve the cooling efficiency. Further, it is preferable that the cooling tower 14 is cooled to a temperature of −50° to −81.8° C. with a cooling pool in order to remove the vapour of a solvent and the like. Further, in order to completely remove vapour of a solvent and the like contained in the acetylene, the acetylene is passed through the absorbing tower 15 in which a porous material such as activated carbon, molecular sieve or silica gel is filled. It is preferable that the absorbing tower 15 is cooled to a temperature of −50° C. to −81.8° C. with a cooling pool.

According to the above-mentioned process, purified acetylene can be prepared in an amount of about 55 to 650 l at standard conditions per one liter of the acetylene absorbing solvent.

The obtained purified acetylene has a purity of 99.99 to 99.9999% by volume.

As the cooling tower 14 and the adsorbing tower 15, any tower can be employed if the towers are efficiently cooled to −50° to −81.8° C. and can collect vapour of a solvent contained in the acetylene. The tower is cooled with ethylene glycol or methanol, and dry ice, and the like.

The above-mentioned process is a process for purifying acetylene in a continuous system. Also, acetylene having a high purity, that is, high purity acetylene can be prepared by a process for purifying acetylene in a batch system.

When the apparatus which is shown in FIG. 3 is employed, purified acetylene can be prepared by the following process.

After acetylene is absorbed into an acetylene absorbing solvent 12 which is contained in an acetylene absorbing and separating tower 22 housing pipe for controlling temperature 23, or while absorbing the acetylene into the acetylene absorbing solvent 12, impurity gases and acetylene contained in the space of the tower 22 are exhausted from an outlet 20 by opening a blowdown valve 21 and then the tower 22 is evacuated with a vacuum pump 24 to remove impurity gases. The temperature of the acetylene absorbing solvent in which acetylene is absorbed is increased with the pipe for controlling temperature 23 and stripped acetylene is passed through the cooling tower 14 and the adsorbing tower 15 to give purified acetylene.

Next, the process for purifying the inside of a dissolved acetylene bomb in which purified acetylene is charged is explained below.

The development a process for purifying the inside of a dissolved acetylene bomb with minimal deterioration of the purity of high purity acetylene having a purity of at least 6N, that is, six-nine, when the high purity acetylene is charged into the bomb has been studied. As a result, it has been found that moisture and impurity gases such as nitrogen gas and oxygen gas which remain or are adsorbed in the space of the bomb, on the mass or on the inside wall of the bomb can be easily exhausted by evacuating with a vacuum pump while heating the bomb and that the bomb is highly purified. Further, the development of a process for purifying the inside of the bomb has been investigated. As a result, it has been found that when a process comprising charging an inert gas such as helium gas or argon gas which does not exert a bad influence upon acetylene such as reaction at the time of being used the acetylene, hydrogen gas which is easily exhausted, highly purified acetylene, the above gases in which moisture is contained or moisture into the bomb and then discharging the gas or the like is repeated to purify the inside of the bomb, the concentration of residual impurity gases contained in the space of the bomb can be not more than several ppm, and the present invention has been accomplished on the basis of the above results.

According to the present invention, the inside of a bomb for acetylene (hereinafter referred to as "bomb") is purified by heating and evacuating the bomb.

In the bomb, a mass, that is, a porous material made of calcium silicate is filled. Since in the space and in the mass of the bomb, moisture remains, it is preferable that the bomb is heated to a temperature suitable for vapourizing the moisture, that is, not less than 105° C. However, when the temperature is more than 250° C., crystallization of calcium silicate occurs and functions of the mass are lowered by the decrease of the porosity. Accordingly, it is suitable that the temperature is 105° to 250° C., preferably 130° to 240° C.

The process for heating or evacuating the bomb can be carried out when the mass is formed or after the mass is formed.

When the bomb is heated, the bomb is evacuated. At that time, it is suitable that the degree of vacuum is adjusted to not more than $1 \times 10^{-1}$ Torr, preferably not more than $5 \times 10^{-2}$ Torr from the viewpoint that impurity gases existing on the surface of the mass or in the mass are exhausted and the purity of the inside of the bomb is improved. Further, it is preferable that the retention time is adjusted to 0.5 to 2 hours in that, although the retention time depends on the kinds and content volume of the bomb.

According to the above process, the inside of the bomb is purified. However, in order to shorten the period of time for purifying the inside of the bomb, it is preferable that after the bomb is evacuated for a prescribed period of time which is usually for 3 to 8 hours, at least one highly purified inert gas selected from the group consisting of helium gas, neon gas, argon gas, krypton gas, xenon gas and radon gas (hereinafter referred to as "inert gas"), hydrogen gas, acetylene gas or the like is charged into the bomb so that the pressure of the bomb is not less than 1 kg/cm$^2$.G, the bomb is allowed to stand for at least 0.5 hours and then the bomb is evacuated. When the bomb is evacuated, it is preferable that the bomb is evacuated to not more than $1 \times 10^{-1}$ Torr, preferably not more than $5 \times 10^{-2}$ Torr. The above process can be repeated in accordance with the purity of the inside of the bomb. Since the purity depends on the kinds and content volume of the bomb, the number of times for repeating the above process cannot be determined. However, in case that high purity acetylene having a purity of not less than 5N is charged into the bomb, it is preferable that the number of times is not less than 4. When the above process is repeated, it is preferable that after the bomb is evacuated for 3 to 8 hours, hydrogen gas having a high purity, highly purified acetylene gas or an inert gas is charged into the bomb.

By the way, a molecule having a large polarity such as H$_2$O, that is, water is firmly adsorbed on the inside wall of the bomb or on the mass since the inside wall of the bomb and the surface of the mass made of calcium silicate have high adsorptivity and are charged with positive electron, and a molecule having a small polarity such as H$_2$ or O$_2$ is easily removed since the molecule has a small adsorption energy. Therefore, when the bomb is heated and evacuated to remove water vapour, impurity gases such as nitrogen gas and oxygen gas as well as water vapour are easily removed at the temperature and under the pressure that water vapour is removed. When the above process is applied, it is confirmed that the bomb is highly purified in a shortened period of time. Accordingly, from the viewpoint of highly purifying the inside of the bomb in a shortened period of time, it is particularly preferable that water is injected into the bomb while the bomb is heated, the bomb is allowed to stand and then the bomb is evacuated or that at least one of hydrogen gas, acetylene gas and inert gas containing moisture instead of the above gas is charged into the bomb, the bomb is allowed to stand and then the bomb is evacuated. The water content in the bomb is not necessarily determined since the water content depends on the kinds and content volume of the bomb. However, it is preferable that the water content is usually 0.05 to 5 mg, more preferably 0.2 to 0.5 mg, per one liter of the content volume of the bomb.

Finally, it is preferable that the bomb which is purified with the above-mentioned gas having a high purity is evacuated to not more than $1 \times 10^{-1}$ Torr, preferably not more than $5 \times 10^{-2}$ Torr, high purity acetylene gas which is the same as the acetylene gas being charged into the bomb is charged while the temperature of the bomb is adjusted to a temperature of not more than the polymerization temperature of acetylene, preferably not more than 60° C. under the pressure of not more than 1.0 kg/cm$^2$.G, and then impurity gases accompanied with the high purity acetylene are discharged from the bomb.

A purified dissolved acetylene bomb is prepared by charging a purified solvent such as DMF or acetone in a prescribed amount into the obtained highly purified bomb.

Next, the process for filling a bomb with high purity acetylene gas is explained below.

According to the present invention, high purity acetylene gas can be charged into a bomb in which a solvent which selectively dissolves acetylene is contained, by thermostatically controlling the temperature of the bomb at a low temperature without any pressing apparatus such as a compressor or a pump.

The high purity acetylene gas which is prepared by the above-mentioned process is charged into a bomb in which a solvent which selectively dissolves acetylene is contained. As the bomb, a dissolved acetylene bomb of which the inside is purified (hereinafter referred to as "high purity acetylene bomb"), that is, a metallic bomb in which a porous material such as calcium silicate, diatomaceous earth, asbestos or charcoal is filled and of which the inside is charged with a solvent which selectively dissolves acetylene in a legal amount, is employed in order to accomodate high purity acetylene.

As the metallic bomb, a steel bomb, an aluminium bomb, a stainless steel bomb, or the like can be employed.

When high purity acetylene is charged into a high purity acetylene bomb, the high purity acetylene bomb is cooled. The cooling temperature depends on the kind of material of the bomb. For example, when a steel bomb is employed, the temperature is adjusted to $-30°$ to $-5°$ C., preferably $-20°$ to $-15°$ C. in order to adjust the charging pressure of the high purity acetylene to not more than 7 kg/cm$^2$.G, and when a stainless steel bomb is employed, the temperature is adjusted to $-78°$ to $-5°$ C., preferably $-78°$ to $-45°$ C. in order to adjust the charging pressure to 2 kg/cm$^2$.G. The difference of the cooling temperature of an aluminium bomb and that of a stainless steel bomb is based upon the difference of the brittleness of the bomb at a low temperature.

The high purity acetylene bomb can be cooled by pouring cooled brackish water onto the surface of the bomb directly or by dipping the bomb into a cooling vessel having a low temperature. It is preferable that the bomb is cooled to a prescribed temperature for about not less than 2 hours before the high purity acetylene gas is charged into the bomb. Examples of a coolant which can be used in the cooling vessel are, for instance, a mixture of ethanol and dry ice, and the like.

As mentioned above, the high purity acetylene is charged into the high purity acetylene bomb with the lowering of pressure which is caused by the lowering of the temperature. At that time, it is suitable that the difference of pressure between the high purity acetylene gas which is charged into a bomb and the internal pressure of the bomb is at most 7 kg/cm$^2$.abs.

According to the present invention, since the purity of high purity acetylene gas is not lowered when the high purity acetylene gas is charged into a high purity acetylene bomb which is sufficiently cooled to a prescribed temperature, the purity and quality of the high purity acetylene are maintained; since the hight purity acetylene gas can be charged into a bomb in a shortened period of time, the labour effectiveness and profitability are improved and since the high purity acetylene gas can be charged into the bomb under a lower pressure, there is little risk for explosive decomposition, and the like and the process is excellent in safety.

The process and apparatus of the present invention are explained below by means of the following Examples. It is to be understood that the present invention is not limited to the Examples, and various changes and modifications may be made in the invention without departing from the spirit and scope thereof.

(Process for providing high purity acetylene gas and the apparatus used in the process)

EXAMPLES 1 TO 4

An apparatus illustrated in FIG. 1 was employed in the procedures of Examples 1 to 4.

As a dissolved acetylene bomb 1, a cylindrical steel vessel having a content volume of 41.0 l was employed. This dissolved acetylene bomb 1 was charged with 14.0 kg of purified acetone which is an acetylene absorbing solvent and then with 550 g of acetylene per one kg of acetone. After the dissolved acetylene bomb 1 was allowed to stand for 24 hours, 20, 40, 60 or 80% by weight of acetylene dissolved in acetone based upon the amount of acetylene charged in the dissolved acetylene bomb 1 was taken out from the dissolved acetylene bomb 1 and the dissolved acetylene bomb 1 was connected with an adsorber 4 by a conduit.

As the adsorber 4, a cylindrical stainless steel vessel having a diameter of 10 cm and a height of 100 cm, in which particles of coconut husk activated carbon having a particle size of from 4 to 8 mesh available from Takeda Chemical Industries, Ltd. as a trade name of Shirasagi G-2C were filled, was employed.

The adsorber 4 was charged with hydrogen gas at a flow rate of 100 ml/min. while the adsorber 4 was heated to a temperature of 300° C. in an isothermal superheater and then the internal air of the adsorber 4 was deaerated with a vacuum pump for three hours before the adsorber 4 was used.

The mixture of acetylene gas and acetone vapour was taken out from the dissolved acetylene bomb 1 and was carried to the adsorber 4 by opening a vessel valve 7 to give refined acetylene.

The obtained refined acetylene was discharged by opening a gas-effluent valve 8 and was analyzed with a Shimadzu G.C. 9A type TCD and FID dual column available from SHIMADZU CORPORATION. The results are shown in Table 3.

EXAMPLES 5 TO 8

The procedure of Examples 1 to 4 was repeated except that as an acetylene absorbing solvent, 17.0 kg of DMF was employed instead of 14.0 kg of acetone and 500 g of acetylene was employed per one kg of DMF. The obtained refined acetylene was analyzed in the same manner as in Examples 1 to 4. The results are shown in Table 3.

COMPARATIVE EXAMPLE 1

The procedure of Example 1 was repeated except that the amount of acetylene discharged was changed into 15% by weight of the charged acetylene to give refined acetylene. The obtained refined acetylene was analyzed in the same manner as in Examples 1 to 4. The results are shown in Table 3.

COMPARATIVE EXAMPLE 2

The procedure of Example 5 was repeated except that the amount of acetylene discharged was changed into 15% by weight of the charged acetylene to give refined acetylene. The obtained refined acetylene was analyzed in the same manner as in Examples 1 to 4. The results are shown in Table 3.

COMPARATIVE EXAMPLE 3

In the procedure of Example 4, after the acetylene dissolved in acetone was discharged in an amount of 80% by weight based upon the amount of the charged acetylene, the residual acetylene in the dissolved acetylene bomb 1 was analyzed in the same manner as in Examples 1 to 4. The results are shown in Table 3.

COMPARATIVE EXAMPLE 4

In the procedure of Example 8, after the acetylene dissolved in DMF was discharged in an amount of 80% by weight based upon the amount of the charged acetylene, the residual acetylene in the dissolved acetylene bomb 1 was analyzed in the same manner as in Examples 1 to 4. The results are shown in Table 3.

TABLE 3

| | | Components of the refined acetylene | | | | | | | |
| Ex. No. | Amount of discharged acetylene (% by weight) | Content of acetylene (% by volume) | Content of acetylene absorbing solvent (ppm) | Content of $N_2$ (ppm) | Content of $O_2$ (ppm) | Content of $H_2$ (ppm) | Content of $CH_4$ (ppm) | Content of CO (ppm) | Content of $CO_2$ (ppm) |
|---|---|---|---|---|---|---|---|---|---|
| 1 | 20 | 99.994 | Acetone was not detected. | 32 | 11 | 1.0 | 12 | 0.05> | 0.2 |
| 2 | 40 | 99.9994 | Acetone was not detected. | 3.2 | 1.0 | 0.1 | 1.5 | CO was not detected. | 0.1 |
| 3 | 60 | 99.9999 | Acetone was not detected. | 0.7 | 0.2 | 0.1> | 0.2 | CO was not detected. | 0.1 |
| 4 | 80 | 99.99995 | Acetone was not detected. | 0.2 | 0.1> | $H_2$ was not detected. | 0.1 | CO was not detected. | 0.1 |
| 5 | 20 | 99.995 | DMF was not detected. | 28 | 9.1 | 1.0 | 11 | 0.05> | 0.2 |
| 6 | 40 | 99.9995 | DMF was was detected. | 3.0 | 0.9 | 0.1 | 1.4 | CO was not detected. | 0.1 |

TABLE 3-continued

| | | | | | | | | | |
|---|---|---|---|---|---|---|---|---|---|
| 7 | 60 | 99.9999 | DMF was not detected. | 0.6 | 0.1 | 0.1> | 0.2 | CO was not detected. | 0.1 |
| 8 | 80 | 99.99995 | DMF was not detected. | 0.2 | 0.1> | $H_2$ was not detected. | 0.1 | CO was not detected. | 0.1 |

| | | Components of refined acetylene | | | | | | | |
|---|---|---|---|---|---|---|---|---|---|
| Com. Ex. No. | Amount of discharged acetylene (% by weight) | Content of acetylene (% by volume) | Content of acetylene absorbing solvent (ppm) | Content of $N_2$ (ppm) | Content of $O_2$ (ppm) | Content of $H_2$ (ppm) | Content of $CH_4$ (ppm) | Content of CO (ppm) | Content of $CO_2$ (ppm) |
| 1 | 15 | 99.93 | Acetone was not detected. | 420 | 120 | 10 | 140 | 0.1 | 0.5 |
| 2 | 15 | 99.94 | DMF was not detected. | 390 | 116 | 10 | 124 | 0.1 | 0.4 |
| 3 | 80 | 97.2 | acetone 27700 | 0.2 | 0.17 | $H_2$ was not detected. | 0.1 | CO was not detected. | 0.1 |
| 4 | 80 | 99.91 | DMF 875 | 0.2 | 0.17 | $H_2$ was not detected. | 0.1 | CO was not detected. | 0.1 |

From the above-mentioned results, it is recognized that each of refined acetylene gases obtained in Examples 1 to 8 contained little acetylene absorbing solvent and had a very high purity.

(Process for purifying acetylene and the apparatus used in the process)

EXAMPLE 9

An apparatus illustrated in FIG. 2 was employed in the procedure of Example 9.

As an acetylene absorbing tower 11, a cylindrical stainless steel tower having a diameter of 10 cm, a height of 50 cm and a content volume of 3925 cm³ was employed. The acetylene absorbing tower 11 was equipped with an opening for introducing acetylene, an opening for returning acetylene absorbing solvent 12 from an acetylene stripping tower 13 and an opening for transferring the acetylene absorbing solvent 12 to the acetylene stripping tower 13, which are sited at the portions of 1 cm, 49 cm and 1 cm above from the bottom of the acetylene absorbing tower 11, respectively. As the acetylene stripping tower 13, a cylindrical stainless steel tower having a diameter of 10 cm, a height of 50 cm and a content volume of 3925 cm³ was employed. The acetylene stripping tower 13 was equipped with an opening for tranferring the acetylene absorbing solvent 12 from the acetylene absorbing tower 11 to the acetylene stripping tower 13 and an opening for returning the acetylene absorbing solvent to the acetylene absorbing tower 11, which were sited at the portions of 49 cm and 1cm above from the bottom of the tower 13, respectively. As a cooling tower 14, a cylindrical stainless steel tower was employed. The tower 14 had a diameter of 2.5 cm and a height of 50 cm and was filled with silica gel. As an adsorbing tower 15, a cylindrical stainless steel tower was employed. The adsorbing tower 15 had a diameter of 2.5 cm and a height of 50 cm and was filled with activated carbon.

The acetylene absorbing tower 11 was cooled so that the temperature of the upper layer of the mixture of DMF and dissolved acetylene in the tower 11 was adjusted to be about −50° C. when the pressure of the acetylene in the dissolved acetylene bomb was reduced to 0.5 kg/cm².G and the acetylene was absorbed by DMF at a rate of 500 l/hour.

The absorbing tower 11 and the acetylene stripping tower 13 were beforehand evacuated to 10⁻¹ Torr and then high purity hydrogen gas (99.9999% by volume) was charged into the absorbing tower 11 and the acetylene stripping tower 13 under a pressure of 0.1 kg/cm².G.

Each of the acetylene absorbing tower 11 and the acetylene stripping tower 13 was charged with 500 ml. of DMF which was an acetylene absorbing agent and then was charged with acetylene at a flow rate of 500 l./hour under a pressure of 0.5 kg./cm².G. After 50 minutes, since the internal pressure of the acetylene stripping tower 13 was lower than that of the acetylene absorbing tower 11 and it was confirmed that these pressures were in a stationary state, a feed valve for adjusting finely a flow rate was opened and adjusted so that the solvent in which acetylene was absorbed was fed from the acetylene absorbing tower 11 to the acetylene stripping tower 13 through the feed valve at a constant flow rate of 55 ml./min. The acetylene absorbing solvent from which acetylene was stripped was transferred from the acetylene stripping tower 13 to the acetylene absorbing tower 11 at a flow rate of 40 ml./min. with a constant rate pump 18.

The absorbing rate of acetylene was very high and most of acetylene charged into the acetylene absorbing tower 11 was dissolved within about 50 minutes. Then an exhaust valve 21 was adjusted so that the internal pressure of the acetylene absorbing tower 11 was 0.2 kg/cm².G, and the pressured excess gas was exhausted to the atmosphere through an integrating flowmeter.

The acetylene absorbing solvent 12 having a temperature of about −50° C. which was transferred to the acetylene stripping tower 13 was heated to about 0° C. which was a temperature when the acetylene absorbing solvent 12 was returned from the tower 13 to the acetylene absorbing tower 11 by flowing a 10% methanol aqueous solution having a temperature of about 15° C. through a heat exchanging pipe 25 of the acetylene stripping tower 13. At that time, the stripped acetylene was transferred from the stripping tower 13 to a cooling tower 14 which was cooled to a temperature of −75° C. with methanol added dry ice as a coolant and vapour of solvent and the like contained in the acetylene were condensed and removed to give purified acetylene. The purified acetylene was carried through an adsorbing tower 15 to absorb and remove the residual impurities and give purified acetylene.

The obtained purified acetylene was analyzed with a Shimadzu G.C. 9A type gas chromatograph TCD and FID automatic change-over detector. As the results, when the detection limit of the analysis was 3.0 ppm, each content of $N_2$, $O_2$ and $CO_2$ was not more than 3 ppm, not more than 2 ppm and not more than 3 ppm, respectively, and the content of CO was not detected, and when the detection limit of the analysis was 1.0 ppm, $PH_3$, $H_2S$ and $AsH_3$ were not detected and the purified acetylene had a purity of 99.999% by volume.

The amount of the purified acetylene which was in a steady state was 425 l./hour (at standard state) and the yield of the purified acetylene based upon the raw acetylene was 85% by volume.

EXAMPLE 10

An apparatus illustrated in FIG. 3 was employed in the procedure of Example 10.

As an acetylene absorbing tower 22, a cylindrical stainless steel tower having a diameter of 10 cm, a height of 50 cm and a content volume of 3925 cm$^3$ was employed. The acetylene absorbing tower 22 was equipped with a temperature control pipe 23 which was sited so as to be dipped into the acetylene absorbing solvent 12, and had an opening for introducing acetylene into the acetylene absorbing tower 22 which was sited at 1 cm above from the bottom of the tower 22. As each of a cooling tower 14 and an adsorbing tower 15, a cylindrical stainless steel tower having a diameter of 2.5 cm, a height of 30 cm and filled with particles of coconut husk activated carbon was employed. The towers were connected together in series.

The acetylene absorbing tower 22 was charged with 1 l. of DMF which was an acetylene absorbing solvent 12 and then was charged with dissolved acetylene at a flow rate of 300 l./hour under a pressure of 0.5 kg./cm$^2$.G while the DMF was cooled by passing a coolant through a temperature control pipe 23 so that the temperature of the DMF was adjusted to $-50°$ C. The exhaust valve 21 was adjusted so that the pressure of the gas phase in the acetylene absorbing tower 22 was 0.2 kg./cm$^2$.G, and pressured excess gas was exhausted to the atmosphere through an integrating flowmeter.

When the acetylene was charged into the acetylene absorbing tower 22 for about one hour, the acetylene absorbing solvent 12 was nearly saturated with the acetylene. Since in the gas phase of the acetylene absorbing tower 11, a large amount of impurity gases which were not easily absorbed into the acetylene absorbing solvent were contained, the acetylene absorbing solvent was recooled to about $-60°$ C. and the gas phase was evacuated to a degree of $10^{-1}$ Torr. with a vacuum pump 24 to remove the impurity gases. Then, the above process for charging argon gas having a high purity into the acetylene absorbing tower 22 and evacuating the gas phase in the acetylene absorbing tower 11 was repeated for 10 times to remove impurity gases contained in the gas phase. After that, the acetylene absorbing solvent was gradually heated to strip out the acetylene which was dissolved in the acetylene absorbing solvent by emptying the temperature control pipe 23.

The obtained stripped acetylene was carried through the cooling tower 14 and absorbing tower 15 which were cooled to about $-75°$ C. in a cooling vessel in which a coolant, that is, methanol added dry ice, was charged to give purified acetylene.

The obtained purified acetylene was analyzed with a Shimadzu G.C. 9A type gas chromatograph TCD and FID automatic change over detector. As the results, when the detection limit of the analysis was 3 ppm, each content of $N_2$, $O_2$ and $H_2$ was less than 3 ppm, respectively, and when the detection limit of the analysis was 1 ppm, each of CO and $CO_2$ was not detected and the purified acetylene had a purity of 99.999% by volume.

The amount of the purified acetylene was 180 l. at a standard state per one batch which required two hours for purifying and the yield based upon the raw acetylene was about 60% by volume.

(Process for purifying the inside of a dissolved acetylene bomb)

EXAMPLE 11

Figure 4:
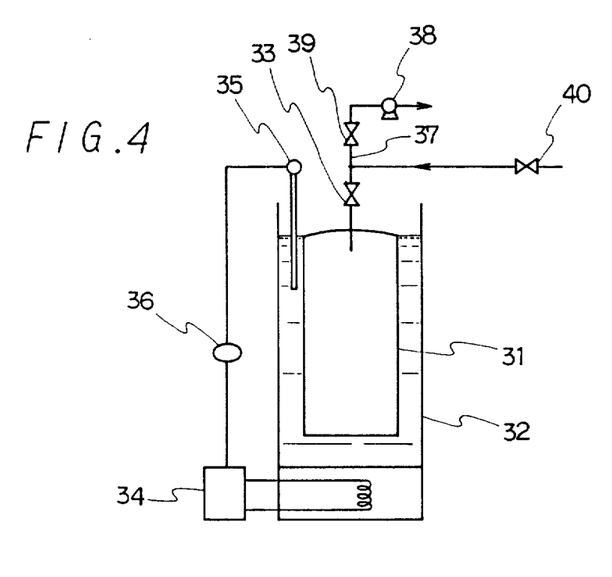
FIG. 4 and FIG. 5 are drawings explaining embodiments of apparatus employed in the process for purifying the inside of a dissolved acetylene bomb of the present invention.

An apparatus illustrated in FIG. 4 was employed in the procedure of Example 11. As a dissolved acetylene bomb 31, a cylindrical vessel having a content volume of 41.0 l and filled with calcium silicate having a porosity of not less than 90% by volume was employed. The dissolved acetylene bomb 31 was dipped in an oil bath 32, and then a vessel valve 33 of the bomb 31 and an intermediate valve 39 were opened. The dissolved acetylene bomb 31 was heated with an oil bath 32 by turning on an electrical current to an electric heater 34. The temperature of the oil in the oil bath 32 was measured with a CA thermocouple 35 and was adjusted to a constant temperature of 200° C. with a temperature recording controller 36.

After that, the gases and steam in the bomb 31 were evacuated with a vacuum pump 38 through a pipe 37 for the periods of time prescribed in Table 4 to give a degree of vacuum of not more than $5 \times 10^{-2}$ Torr. In each of the experiments, a new dissolved acetylene bomb was employed.

The bomb 31 was charged with 16 kg. of purified DMF having a purity of 99.9999% by volume by closing the intermediate valve 39 and opening the value 40 and then was charged with high purity acetylene gas having a purity of 99.9999% by volume so that the pressure of gases in the bomb 31 was 2 kg./cm$^2$.G. After the valve 40 was closed and the bomb 31 was allowed to stand for 24 hours at room temperature, that is, about 20° C., the vessel valve 33 and the intermediate valve 39 were opened and the gases in the bomb 31 were discharged through the pipe 37 with a vacuum pump so that the pressure of gases in the bomb 31 was 0.1 kg./cm$^2$.G. Then, the bomb 31 was charged again with high purity acetylene gas so that the pressure of the gases in the bomb 31 was 2 kg./cm$^2$.G, and the bob 31 was allowed to stand for 24 hours at room temperature. After that, the gases contained in the bomb 31 were analyzed. The results are shown in Table 4.

TABLE 4

| Preparation Example No. | Evacuated period of time (hours) | Content of impurity gases (ppm) | | |
|---|---|---|---|---|
| | | $N_2$ | $O_2$ | $CO_2$ |
| 1 | 140 | 9 | 1.0 | N.D. |
| 2 | 160 | 4 | 1.0> | N.D. |
| 3 | 180 | 1.5 | N.D. | N.D. |
| 4 | 200 | N.D. | N.D. | N.D. |

Note:
Detection limit is 1.0 ppm.

EXAMPLE 12

Figure 5:
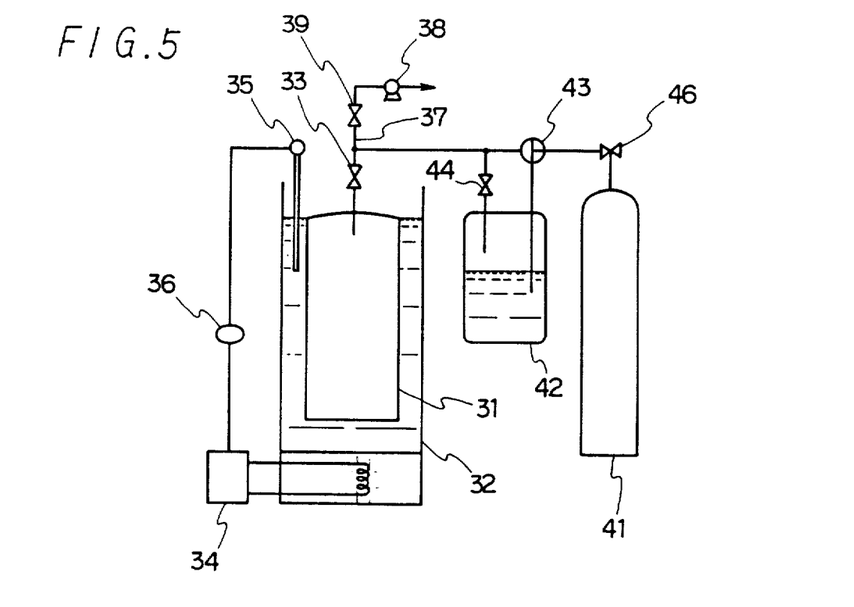

An apparatus illustrated in FIG. 5 was employed in the procedure of Example 12. As a dissolved acetylene bomb 31, a cylindrical vessel having a content volume of 41.0 l and filled with calcium silicate having a porosity of not less than 90 % by volume was employed. The acetylene bomb 31 was dipped into an oil bath 32 and then a vessel valve 33 and an intermediate valve 39 were opened. The dissolved acetylene bomb 31 was heated with the oil bath 32 by turning on an electric current to an electric heater 34. The temperature of the oil bath was measured with a CA thermocouple 35 and was adjusted to a constant temperature of 200° C. with a temperature recording controller 36.

After that, the gases and steam in the bomb 31 were exhausted with a vacuum pump 38 through a pipe 37 for 8 hours with a rotary pump having an ability to evacuate to a degree of vacuum of $1 \times 10^{-2}$ Torr. Then, the intermediate valve 39 was closed and a vessel valve 46 was gradually opened and a three-way cock 43 was opened so as to connect the bomb 31 with the bomb 41 in which high purity hydrogen gas was filled. The bomb 31 was charged with high purity hydrogen gas having a purity of 99.9999% by volume from the bomb 41 in which high purity hydrogen gas was filled so that the inner pressure of the bomb 31 was 2 kg./cm².G at a temperature of 20° C. At that time, a valve 44 was closed. After the valve 33 and the three-way cock 43 were closed, the bomb 31 was allowed to stand for 2 hours. Then, the valve 33 and the intermediate valve 39 were opened, and the bomb 31 was evacuated again with the vacuum pump 38.

The above procedure that charging hydrogen gas having a high purity into the bomb 31, allowing the bomb 31 to stand and evacuating the bomb 31 was employed as one cycle of the procedure. The cycle of the above procedure was repeated several times as is shown in Table 5 at intervals of 12 hours. After each cycle was repeated, the gases in the bomb 31 were analyzed with a Shimadzu G.C. 9A type gas chromatograph TCD and FID automatic change-over detector, and the contents of impurity gases in the hydrogen gas were measured. The results are shown in Table 5.

TABLE 5

| Cycle (times) | Contents of impurity gases | | |
|---|---|---|---|
| | N₂ (ppm) | O₂ (ppm) | CO₂ (ppm) |
| 1 | 6800 | 1600 | 20 |
| 4 | 5.0 | 1.0> | 1.0> |
| 6 | 2.0 | N.D. | N.D. |
| 8 | 1.0> | N.D. | N.D. |
| 10 | N.D. | N.D. | N.D. |

Note:
Detection limit is 1.0 ppm.

After the cycles of above-mentioned procedure was repeated 10 times, the bomb 31 was filled with 16.0 kg. of purified DMF having a purity of 99.9999% by volume and then was charged with high purity acetylene gas having a purity of 99.9999% by volume to attain an internal pressure of the bomb 31 of 2.0 kg./cm².G. After the bomb 31 was allowed to stand for 24 hours at room temperature, that is , about 20° C., the bomb 31 was evacuated to a pressure of 0.1 kg./cm².G. The bomb 31 was charged again with the high purity acetylene gas to attain an internal pressure of the bomb 31 of 2.0 kg./cm².G. After the bomb 31 was allowed to stand for 24 hours at room temperature, that is, about 20° C., the gases in the bomb 31 were analyzed and the process for cleaning the bomb was finished. As the result, the contents of impurity gases such as nitrogen gas, oxygen gas and CO₂ gas were not more than the detection limit, that is, not more than 1.0 ppm.

EXAMPLE 13

An apparatus illustrated in FIG. 5 was employed in the procedure of Example 13. The procedure of Example 12 was repeated except that the procedure that the bomb 31 was directly charged with high purity hydrogen gas having a purity of 99.9999% by volume from the bomb 41 in which the high purity hydrogen gas was filled was changed into a procedure that the bomb 41 was connected with a vessel 42 in which pure water was filled by opening the three-way cock 43 and then the valve 44 was opened to charge hydrogen gas into the vessel 42 and to introduce hydrogen gas containing moisture having an absolute humidity of about 1.0% into the bomb 31. After the above-mentioned procedure was repeated several times, the impurity gases in the hydrogen gas were analyzed in the same manner as in Example 12. The results are shown in Table 6.

TABLE 6

| Cycle (times) | Contents of impurity gases | | |
|---|---|---|---|
| | N₂ (ppm) | O₂ (ppm) | CO₂ (ppm) |
| 1 | 4650 | 1260 | 12 |
| 4 | 3.0 | 1.0> | 1.0> |
| 6 | 1.0 | N.D. | N.D. |
| 8 | N.D. | N.D. | N.D. |

Note:
Detection limit is 1.0 ppm.

After the above-mentioned procedure was repeated 8 times, the bomb 31 was filled with 16.0 kg. of the refined DMF having a purity of 99.9999% by volume and then was charged with high purity acetylene gas having a purity of 99.9999% by volume to attain an internal pressure of the bomb 31 of 2.0 kg./cm².G. After the bomb 31 was allowed to stand for 24 hours at room temperature, that is, 20° C., the bomb 31 was evacuated to a pressure of 0.1 kg/cm².G. The bomb 31 was charged again with the high purity acetylene gas to attain an internal pressure of the bomb 31 of 2.0 kg/cm².G. After the bomb 31 was allowed to stand for 24 hours at room temperature, that is, about 20° C., the gases in the bomb 31 were analyzed and thereby the procedure for cleaning was finished. As the result, the contents of impurity gases such as nitrogen gas, oxygen gas and CO₂ gas were not more than the detection limit, that is, not more than 1.0 ppm.

(Process for charging high purity acetylene into a bomp)

EXAMPLE 14

Figure 6:
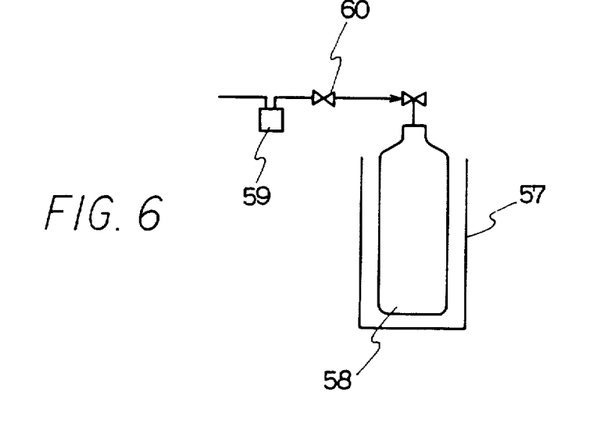
FIG. 6 is a drawing explaining an embodiment of a process for filling a bomb with high purity acetylene of the present invention.

An apparatus illustrated in FIG. 6 was employed in the procedure of example 14. As a dissolved high purity acetylene bomb 58, a steel bomb having a content volume of 10 l was employed. The bomb 58 was dipped into a cooling vessel 57 which was cooled to a temperature of −20° C. with a coolant, that is, ethanol added dry ice. The refined acetylene obtained in Example 10 was charged into the bomb 58 through a flowmeter 59 and a valve 60 at a flow rate of 0.3 kg/hour. The period of time for charging the acetylene and amount of the acetylene gas charged into the bomb 58 were measured. The results are shown in Table 7.

The dissolved high purity acetylene bomb 58 was beforehand treated with the following procedure. That is, the bomb 58 was beforehand evacuated for 24 hours at a temperature of 250° C. to 300° C. in a constant temperature oven, and the bomb 58 was cooled to ordinary temperature and was charged with DMF in a content of 43.7% by volume based upon the content volume of the bomb 58 with the pressure of hydrogen gas having a high purity. After the bomb 58 was evacuated with a vacuum pump, the bomb was charged with high purity acetylene so that the internal pressure was 0.2 to 0.5 kg/cm$^2$.G at room temperature, and the bomb 58 was cooled to −20° C., and then the bomb 58 was allowed to stand for 2 hours.

EXAMPLE 15

The procedure of Example 14 was repeated except that the cooling vessel 57 was cooled to a temperature of −55° C. with dry ice and ethyl alcohol, that as a dissolved acetylene bomb, an aluminium bomb having a content volume of 10 l. was employed and that the flow rate of acetylene was changed into 1.5 kg/hour. The period of time for charging the acetylene and the amount of the acetylene gas charged into the bomb 58 were measured. The results are shown in Table 7.

COMPARATIVE EXAMPLE 5

The procedure of Example 14 was repeated except that the cooling vessel 57 was not employed, which is a conventional process for charging acetylene into a bomb 58. The atmospheric temperature around the bomb 58 when acetylene was charged into a bomb 58 was 10.4° C. The period of time for charging the acetylene and the amount of the acetylene gas charged into the bomb 58 were measured. The results are shown in Table 7.

TABLE 7

| Example No. | Change of charging pressure and charged amount of acetylene with the passage of time [Upper column: charging pressure (kg/cm$^2$ · G); Lower column: charged amount (kg)] | | | | | | |
|---|---|---|---|---|---|---|---|
| | After 30 min. | After 60 min. | After 90 min. | After 120 min. | After 150 min. | After 180 min. | After 450 min. |
| 14 | 0.6 | 1.3 | 2.4 | 3.6 | 5.0 | 6.6 | — |
|  | 0.3 | 0.6 | 0.9 | 1.2 | 1.5 | 1.8 | — |
| 15 | 0.3 | 0.5 | 1.1 | — | — | — | — |
|  | (After 72 min. which is end point.) | | | | | | |
|  | 0.75 | 1.5 | 1.8 | — | — | — | — |
| Comparative Example 5 | 1.6 | 3.3 | 4.9 | 6.5 | 8.2 | 9.8 | 23.5 |
|  | 0.12 | 0.24 | 1.36 | 0.48 | 0.6 | 0.72 | 1.8 |

From the above-mentioned results, it is recognized that in accordance with the process of the present invention, acetylene gas having a high purity can be more efficiently charged into an acetylene bomb in a shortened period of time under a condition of lower pressure than the conventional process.

The procedure of Comparative Example 1, that is, a conventional process was carried out in a lower atmospheric temperature, that is, 10.4° C. However, when the procedure is carried out in a higher atmospheric temperature, e.g., in summer, there is a necessity that the temperature of a solvent and a bomb are raised and the solubility of acetylene to a solvent is lowered. Therefore, it is required for not only charging acetylene under higher pressure but also decreasing the amount of the charged acetylene or extending the period of time for charging acetylene.

What is claimed is:

1. A process for providing high purity acetylene gas, comprising discharging high purity acetylene gas from a dissolved acetylene bomb and removing a solvent which is accompanied with the high purity acetylene gas by passing the high purity acetylene gas through an adsorbent when the acetylene is used.

2. The process for providing high purity acetylene of claim 1, wherein said bomb is a bomb prepared by charging high purity acetylene and then discharging the acetylene in an amount of 20 to 80% by weight of the acetylene which is charged in the bomb.

3. The process for providing high purity acetylene of claim 2, wherein the inside of said bomb is purified before said bomb is charged with acetylene and a solvent.

4. The process for providing high purity acetylene of claim 1, wherein said adsorbent is coconut husk activated carbon.

5. A process for purifying acetylene, comprising absorbing acetylene into a solvent having a temperature of −20° to −81.8° C., heating the solvent containing the acetylene to a temperature of −10° to +20° C. to strip acetylene from the acetylene absorbing solvent, passing the stripped acetylene through a packed bed in which a porous material is filled to adsorb solvent contained in said stripped acetylene and then passing the stripped acetylene through a filter for removing superfine powders of impurities.

6. The process for purifying acetylene of claim 5, wherein said solvent is acetone, N,N-dimethylformamide, N-methylpyrrolidone or an admixture thereof.

7. The process for purifying acetylene of claim 5, wherein the absolute pressure of acetylene when the acetylene is absorbed into the solvent is 0.1 to 7.0 kg/cm$^2$.

8. A process for purifying the inside of a dissolved acetylene bomb for storing acetylene, comprising heating a dissolved acetylene bomb and evacuating the dissolved acetylene bomb.

9. The process for purifying the inside of a dissolved acetylene bomb of claim 8, including a process for filling the evacuated dissolved acetylene bomb with at least one member selected from the group consisting of hydrogen gas, acetylene gas, water vapor, helium gas, neon gas, argon gas, krypton gas, xenon gas and radon gas, allowing to stand the dissolved acetylene bomb and then evacuating the dissolved acetylene bomb.

10. The process for purifying the inside of a dissolved acetylene bomb of claim 9, comprising after filling the dissolved acetylene bomb with high purity acetylene gas, the step of evacuating the dissolved acetylene bomb as a last process for purifying.

11. A process for filling a bomb with high purity acetylene gas, comprising thermostatically controlling the temperature of a bomb at a low temperature to fill the bomb with acetylene gas without any pressure when filling a bomb in which a solvent which selectively dissolves acetylene is charged, with high purity acetylene gas.

12. The process for filling a bomb with high purity acetylene gas of claim 11, wherein said bomb is a steel bomb, an aluminium bomb or a stainless steel bomb, and the thermostatically controlled temperature is −30° to −5° C. when said bomb is a steel bomb and the thermostatically controlled temperature is −78° to −5° C. when said bomb is an aluminium bomb or a stainless steel bomb.

13. An apparatus for purifying high purity acetylene gas, comprising a metallic bomb containing a porous material for holding high purity acetylene gas and a solvent to selectively dissolve the acetylene gas, an adsorber connected to said metallic bomb for adsorbing the solvent associated with the acetylene when the acetylene is withdrawn from said metallic bomb, and a filter connected to a discharging end of said adsorber for removing superfine powders of impurities from the acetylene.

14. An apparatus for purifying acetylene, comprising an acetylene absorbing tower for absorbing acetylene into a solvent which selectively absorbs acetylene at −20° to −81.8° C., means for transferring solvent-dissolved acetylene from the acetylene absorbing tower to an acetylene stripping tower for stripping the acetylene from the solvent at −10° to +20° C., means for transferring the stripped acetylene from said stripping tower to an adsorbing tower, said adsorbing tower containing porous materials for removing impurities included in the stripped acetylene, means for transferring the acetylene from said adsorbing tower to a filter, said filter removing superfine powders of impurities from said acetylene, and means for returning the solvent form which the acetylene is stripped from the acetylene stripping tower to the acetylene absorbing tower.

* * * * *